(12) United States Patent
Thakur et al.

(10) Patent No.: US 7,141,411 B2
(45) Date of Patent: Nov. 28, 2006

(54) DECAFFEINATING MICROORGANISM AND PROCESS OF BIO-DECAFFEINATION OF CAFFEINE CONTAINING SOLUTIONS

(75) Inventors: Munna Singh Thakur, Mysore (IN); Renu Sarath Babu Vegesna, Mysore (IN); Naikankatte Ganesh Karanth, Mysore (IN); Mandyam Chakravarathy Varadaraj, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 345 days.

(21) Appl. No.: 10/400,311

(22) Filed: Mar. 27, 2003

(65) Prior Publication Data
US 2004/0191333 A1    Sep. 30, 2004

(51) Int. Cl.
*C07G 17/00*    (2006.01)
*C12P 1/04*    (2006.01)

(52) U.S. Cl. .................... 435/267; 435/170; 435/253.3

(58) Field of Classification Search .................... None
See application file for complete search history.

(56) References Cited

U.S. PATENT DOCUMENTS 4,228,191 A * 10/1980 Haas et al. .................... 426/45

FOREIGN PATENT DOCUMENTS

CH    626781    12/1981

OTHER PUBLICATIONS

Lee, et al., "Decaffeination of Coffee Beans".

* cited by examiner

*Primary Examiner*—Irene Marx
(74) *Attorney, Agent, or Firm*—Winstead Sechrest & Minick P.C.

(57) ABSTRACT

The present invention relates to a simple, safe, and efficient process for the complete bio-decaffeination of caffeine-containing solutions using fungus *Pseudomonas alcaligenes* CFR 1708, a method of isolating *pseudomonas alcaligenes* CFR 1708 useful for the bio-decaffeination of caffeine-containing solutions, a *Pseudomonas alcaligenes* strain of accession number CFR 1708, and a decaffeinated solution obtained by aforementioned process.

9 Claims, 1 Drawing Sheet

Figure 1:
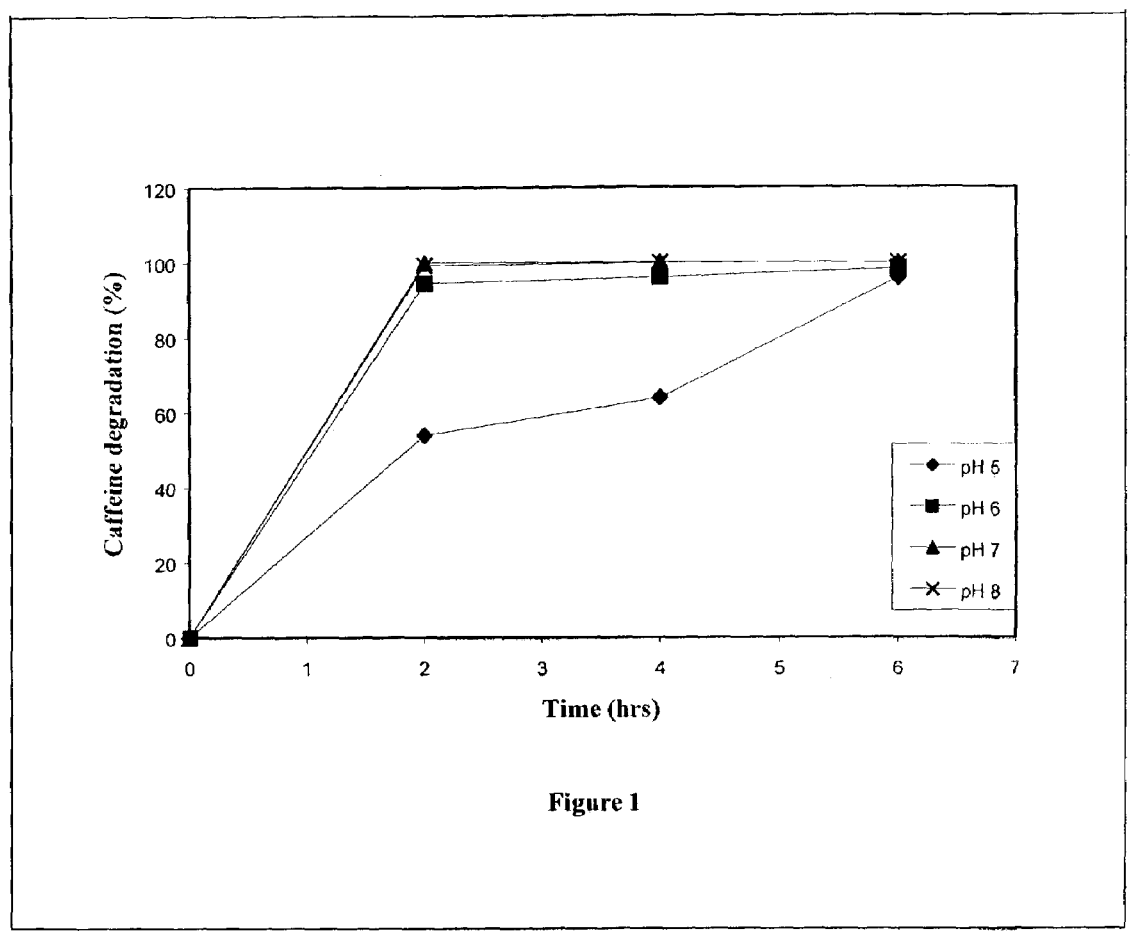

DECAFFEINATING MICROORGANISM AND PROCESS OF BIO-DECAFFEINATION OF CAFFEINE CONTAINING SOLUTIONS

FIELD OF THE PRESENT INVENTION

The present invention relates to a simple, safe, and efficient process for the complete bio-decaffeination of caffeine-containing solutions using fungus *Pseudomonas alcaligenes* CFR 1708, a method of isolating *pseudomonas alcaligenes* CFR 1708 useful for the bio-decaffeination of caffeine-containing solutions, a *Pseudomonas alcaligenes* strain of accession number CFR 1708, and a decaffeinated solution obtained by aforementioned process.

BACKGROUND AND PRIOR ART OF THE PRESENT INVENTION

Caffeine ($C_8H_{10}N_4O_2$) is an alkaloid naturally occurring in coffee and coca beans cola nuts and tea leaves. Caffeine is described as a methylated xanthine alkaloid derivative (1,3–7 Trimethyl xanthine). Caffeine is water soluble above 175° F. and is soluble in methanol, ethanol etc. In mammals ingested caffeine is rapidly absorbed, metabolized and excreted in the urine as methyl Xanthine derivatives. Caffeine is mildly stimulating and is used as a therapeutic agent.

Caffeine has become a ubiquitous drug. Caffeine is widely distributed in pharmaceutical preparations and beverages. It has a variety of biological effects. It stimulates the central nervous system, shows toxicity when fed excessively and is even mutagenic in-vitro. Theobromine shows caffeine like pharmacological activities but does not cause excessive reaction as caffeine, so used as diuretic.

Many of the physiological effects of coffee beverage are due to their caffeine content. Dr. Karal Wimmer of Germany invented the process of removing caffeine from coffee. This process is known as decaffeination and the product is known as "Caffeine free Coffee" Reference may be made to the work on *Coffee Solubilization: Commercial Processes* and *Techniques*, Pintauro and Nicholas, D., (1975), wherein they have used methylene chloride for decaffeination of coffee. The drawback of this process is that the flavor elements and oil are drawn off from the beans; presence of residual solvent, which is not safe for human health and the time taken for the whole process, is more than 24 hours.

Reference may be made to the work of Zeller and Saleeb, *Proceedings of 18th ASIC Colloquium (Helsinki)*, 168–172, (1999), wherein they have reported decaffeination of coffee beans using Ethyl Acetate. The drawback of this method is, it involves the use of organic solvent, which makes the process hazardous to health, expensive, time consuming and highly labour intensive.

Reference may be made to Hinman and Saleeb (1984), (General Foods Corp.), European Patent No.: EP-0140269, *Coffee Technology;* wherein they have reported the decaffeination of coffee by Charcoal or carbon. The drawbacks of this process are loss of flavor elements and colour, presence of residual caffeine in the product in addition to the longer time duration involved in the whole process.

Reference may be made to a patent by General Foods Corporation, USA, (1973), U.S. Pat. No.: Br. 1,313,047, *Coffee Technology*, wherein they have reported the use of Triglycerides. The drawbacks of this process are the loss of flavor and incomplete removal of caffeine from the final product.

Reference may be made to the work of Katz, S. N, *Coffee Technology*, (1987), wherein he has reported the use of supercritical $CO_2$ for decaffeination. The drawback of this process is that although it does not affect the quality of the final product, it necessitates the extraction of caffeine to the surface of the bean by steam and involves very high costs and the caffeine is not completely removed from the final product.

Reference may be made to the work of Michael Gluck and Franz Lingens (1987), *Applied Microbiology and Biotechnology*, 334–340, on the studies on microbial production of theobromine and heteroxanthine from caffeine wherein they have used a strain of *Pseudomonas putida*. The drawbacks of this process are that the cells grow very slow in the medium containing caffeine, degradation of caffeine was very slow and the accumulation of products was too low for commercial purposes and the products produced in this process have effects similar to that of caffeine.

Reference may be made to the work of Wouter J. Middlehoven and Cor. M Bakker (1982) *Eur. J Appl. Microbio. Biotechnol.* 214–217, wherein they have reported the degradation of caffeine by immobilized cells of *Pseudomonas putida* strain C 3024 wherein they have immobilized the cells in beads of agar. The disadvantages of the process are the immobilization method tends to remove substances other than caffeine thus adversely affecting the flavor of roasted coffee and the growth yields of the cells are very low.

Reference may be made to a Swiss patent by Robert, F. D., Nestle Group (1981) Patent No. CH626781 "Decaffeination process" on decaffeination of vegetable material when exposed to the microorganism of the species *Acinetobacter*. The disadvantage of this method is that caffeine removal from the coffee extract is very slow and only about half of the initial caffeine content is removed from the extract.

Reference may be made to U.S. Pat. No. 4,228,191 (1980) wherein they have reported the use cell free extracts of *Pseudomonad* like organisms for decaffeination of aqueous caffeine containing liquids such as coffee extract. The disadvantage is the requirement of addition of cofactors for decaffeination, which are highly unstable.

OBJECTS OF THE PRESENT INVENTION

The main object of the present invention is to develop a simple, safe, and efficient process for the complete bio-decaffeination of caffeine-containing solutions using fungus *Pseudomonas alcaligenes* CFR 1708.

Another main object of the present invention is to decaffeinate caffeine-containing solution of high caffeine concentration.

Yet another object of the present invention is to develop a method for complete caffeine degradation.

Still another object of the present invention is to develop a process for quick and efficient decaffeination Another main object of the present invention is to develop a method of isolating *pseudomonas alcaligenes* CFR 1708 useful for the bio-decaffeination of caffeine-containing solutions.

Another main object of the present invention is to isolate a *Pseudomonas alcaligenes* strain of accession number CFR 1708.

Another main object of the present invention is to develop a decaffeinated solution using aforementioned process.

Another main objective of the present invention is to provide "a process for the bio-decaffeination of solutions containing caffeine", which obviates the drawbacks detailed above.

Another objective of the present invention is to isolate microorganisms, which possess decaffeination activity.

Still another object of the present invention is to prepare inoculum of microbial cultures for effective decaffeination.

Yet another object of the present invention is to prepare a caffeine-containing medium suitable for the growth of the organism.

Another object of the present invention is to optimize conditions for effective degradation of caffeine in solution.

SUMMARY OF THE PRESENT INVENTION

The present invention relates to a simple, safe, and efficient process for the complete bio-decaffeination of caffeine-containing solutions using fungus *Pseudomonas alcaligenes* CFR 1708, a method of isolating *pseudomonas alcaligenes* CFR 1708 useful for the bio-decaffeination of caffeine-containing solutions, a *Pseudomonas alcaligenes* strain of accession number CFR 1708, and a decaffeinated solution obtained by aforementioned process.

DETAILED DESCRIPTION OF THE PRESENT INVENTION

Accordingly, the present invention relates to a simple, safe, and efficient process for the complete bio-decaffeination of caffeine-containing solutions using fungus *Pseudomonas alcaligenes* CFR 1708, a method of isolating *pseudomonas alcaligenes* CFR 1708 useful for the bio-decaffeination of caffeine-containing solutions, a *Pseudomonas alcaligenes* strain of accession number CFR 1708, and a decaffeinated solution obtained by aforementioned process.

In an embodiment of the present invention, wherein a simple, safe, and efficient process for the complete bio-decaffeination of caffeine-containing solutions using fungus *Pseudomonas alcaligenes* CFR 1708, said process comprising steps of:
culturing the fungus in caffeine agar plates,
transferring actively growing culture into nutrient broth containing 0.1–0.5 g/L caffeine,
incubating culture of step (b) at about 28–30° C. for about 20–24 hrs under agitation of between about 50–200 rpm to obtain pre-inoculum,
transferring the pre-inoculum to nutrient broth comprising about 0.5–2 g/L caffeine,
incubating the pre-inoculum at about 28–30° C. for about 20–24 hours under agitation between about 50–200 rpm to accumulate biomass,
harvesting the biomass by centrifugation for about 10–20 min at about 10,000–16,000 g at temperature ranging between about 0–4° C. to obtain pellet,
inducing the pellet for caffeine degradation by aseptically transferring the pellet into sterilized caffeine liquid medium of pH about 5–9,
incubating the induced pellet at about 25–35° C. under agitation between about 50–200 rotations per minute for time duration of about 36–60 hours, and
decaffeinating caffeine-containing solution by incubating with the pellet of step (h).

In another embodiment of the present invention, wherein concentration of caffeine in nutrient broth is ranging between 0.2–0.4 g/L.

In yet another embodiment of the present invention, wherein the sterilized caffeine liquid medium comprises about 40–60 g/L of disodium hydrogen orthophosphate septahydrate, about 10–15 g/L of potassium dihydrogen orthophosphate, about 1–5 g/L of sodium chloride, about 2–7 g/L ammonium chloride, and about 0.1–0.5 g/L Caffeine.

In still another embodiment of the present invention, wherein the induction time is ranging between about 40–48hr.

In still another embodiment of the present invention, wherein the concentration of caffeine in caffeine-containing solution is ranging between about 0.01–5 g/L of caffeine.

In still another embodiment of the present invention, wherein the caffeine degradation is complete in about 1–14 hours.

In still another embodiment of the present invention, wherein incubating at temperature ranging between 28–30° C.

In still another embodiment of the present invention, wherein the nutrient broth comprises about 0.5–4 g/L of yeast extract, about 3–8 g/L of peptone, about 3–8 g/L of sodium chloride, and about 0.08–0.7 g/L of caffeine.

In still another embodiment of the present invention, wherein the decaffeination effect improves with increase in pH from 5 to 9.

In another embodiment of the present invention, wherein a method of isolating *pseudomonas alcaligenes* CFR 1708 useful for the bio-decaffeination of caffeine-containing solutions, said method comprising steps of:
mixing soil sample comprising microbes obtained from coffee processing units with caffeine liquid medium to obtain a culture,
incubating the culture for about 70–74 hr at about 28–30° C. in a shaker at 140–160 rpm,
making serial dilutions of the above grown culture,
inoculating diluted cultures into caffeine agar medium petri plates,
incubating the inoculated plates at about 35–39° C. for about 1–3 days, and
isolating the well-separated colonies of the caffeine degrading bacteria growing on the incubated plates to obtain pure cultures, In still another embodiment of the present invention, wherein the caffeine liquid medium comprises about 40–60 g/L of disodium hydrogen orthophosphate septahydrate, about 10–15 g/L of potassium dihydrogen orthophosphate, about 1–5 g/L of sodium chloride, about 2–7 g/L ammonium chloride, and about 0.1–0.5 g/L Caffeine.

In still another embodiment of the present invention, wherein the serial dilutions are ranging between $10^{-1}$ to $10^{-9}$.

In another main embodiment of the present invention, wherein a *Pseudomonas alcaligenes* strain of accession number CFR 1708.

In still another embodiment of the present invention, wherein the characteristics of the strain are as given below with sign+shows Positive for growth, and sign−shows negative for growth.

| Cultural and biochemical tests for the identification of the isolate. | |
|---|---|
| Biochemical Test | Result |
| Catalase | + |
| Oxidase | − |
| Nitrate reduction | − |
| Indole Production | − |
| Methyl red test | − |

-continued

Cultural and biochemical tests for the identification of the isolate.

| Biochemical Test | Result |
|---|---|
| Voges Proskauer test | − |
| Starch hydrolysis | − |
| Citrate utilization | + |
| Oxidation | + |
| Fermentation | + |
| Motility | + |
| Malonate Utilization | + |
| Arginine dihydrolase | + |
| Gelatin hydrolysis | − |
| Growth at 41° C. | + |
| Growth at 4° C. | − |
| Acid slant | − |
| Acid butt | − |
| Alkaline slant | + |
| Alkaline butt | + |
| H2S production | + (Weak) |
| Gas production | − |
| Urease | + |
| Dextrose utilization | − |
| Mannitol utilization | − |
| Polyhydroxy alkanoate (PHB) accumulation | − |

In still another embodiment of the present invention, wherein a decaffeinated solution obtained by aforementioned process.

In still another embodiment of the present invention, wherein the present invention is related to a process for the bio-decaffeination of solutions containing caffeine.

In still another embodiment of the present invention, wherein the main utility of the invention is the complete degradation of caffeine at neutral pH and room temperature in a simple medium and can be used for the decaffeination of solutions containing caffeine.

In still another embodiment of the present invention, wherein the novelty of the present invention is to completely degrade caffeine rapidly and completely using a microbial culture grown in a synthetic liquid medium.

BRIEF DESCRIPTION OF THE ACCOMPANYING DRAWINGS

FIG. 1 shows % caffeine degradation with respect to time

In the drawing accompanying this specification FIG. 1 represents the HPLC data of the degradation of caffeine by the culture.

Accordingly the present invention provides for a process for the bio-decaffeination of caffeine containing solutions, which comprises:

1. A process for the Bio-decaffeination of Caffeine Containing Solutions which Comprises:
a) isolating the microorganism by:
  i) mixing one gram of soil sample which may be collected from coffee processing units with 100 ml of caffeine liquid medium in a 250 ml flask,
  ii) incubating for a period ranging from 68–76 hr at 24–34° C. may be effected in an orbital rotary shaker set at 130–170 rpm,
  iii) preparing and pouring caffeine agar medium may be effected in petri plates,
  iv) making ten-fold serial dilutions ($10^{-1}$ to $10^{-9}$) of the above grown culture,
  v) inoculating 0.04–0.2 ml of the dilutions may be effected on to each plate,
  vi) incubating at a temperature in the range of 32–40° C. for a period of 1–4 days,
  vii) selecting and further purifying the isolated colonies may be effected by growing on the above plates to obtain pure cultures,
  viii) aseptically selecting and transferring the well-separated colonies of the caffeine degrading bacteria formed on incubated caffeine agar plates may be effected on basis of colony morphology into fresh caffeine agar plates and incubating in the range of 26–34° C. for 68–76 hr and
  ix) maintaining the organism by subculturing may be effected on caffeine agar slants at regular intervals of 25–35 days.
b) identifying the organism as *Pseudomonas alcaligenes* CFR 1708 may be based on the morphological characteristics:
  i) gram negative coccobacilli forming round, small, raised and smooth colonies,
  ii) positive for production of catalase, alkaline slant and butt, hydrogen sulphide and urease,
  iii) negative for production of oxidase, indole, Acid slant and butt, gas and polyhydroxy alkanoate,
  iv) positive for citrate utilization, oxidation, fermentation of sugars, motility, malonate utilization, arginine dihydrolase activity, growth at 41° C.,
  v) negative for nitrate reduction, methyl red test, voges proskauer test, starch hydrolysis, gelatin hydrolysis, growth at 4° C. dextrose utilization and mannitol utilization
c) developing a pre-inoculum may be effected by transferring a loop full of actively growing culture of *P. alcaligenes* on nutrient agar fortified with 0.08–0.7 g/L caffeine to 40–110 ml of nutrient broth containing 0.08–0.7 g/L caffeine,
d) incubating in the range of 24–36° C. for a period of 18–26 hr may be effected under agitation between 40–210 rpm.
e) transferring 40–110 ml of the 16–26 hrs grown pre inoculum may be effected to 0.8–0.22 L of nutrient broth containing 0.1–5 g/L caffeine and incubation at 26–32° C. for 18–26 hours under agitation between 40–210 rpm.
f) harvesting the biomass accumulated after 18–26 hours may be effected by centrifugation for 8–22 min in a bench-top refrigerated centrifuge at 8,000–18,000 g at 0–60° C. to obtain the wet biomass as a pellet.
g) inducing the above biomass for caffeine degradation may be effected by aseptically transferring the biomass pellet into a 500 ml flask containing 40–160 ml of sterilized caffeine liquid medium and incubation in a range of 26–32° C. under agitation between 40–210 rotations per minute for a period of 38–50 hours.
h) decaffeination using the biomass thus induced for caffeine degradation may be done by addition of 0.5–4 gram wet weight of this biomass to the caffeine, liquid medium containing 0.1–3 g/L caffeine and incubation for period of 1–14 hr.
i) drawing of 0.5–2 ml aliquots of samples from the flasks at desired intervals of time and subjecting them to centrifugation at 8,000–17,000 g for a period of 8–17 minutes.
j) analysis of the supernatants of the centrifuged culture broth samples drawn at different intervals of time for residual caffeine may be performed by High Performance Liquid Chromatography using a $C_{18}$ column with a mixture of Water and Aetonitrile in the ratio of 80:20–90:10 as the mobile phase with an isocratic elution at a flow rate of 0.5–1.5 ml/min, with an ultraviolet-visible Spectrophotometric detector set at 273 nm.

In an embodiment of the present invention, the age of the culture slant may be selected from 0.5–4 weeks and the age of the inoculum may be 10–20 hours grown under agitation at 40–210 rpm.

In yet another embodiment of the present invention, the nutrients employed in the cultivation may include 0.5–4 g/L of yeast extract, 3–8 g/L of peptone, 3–8 g/L of sodium chloride and 0.08–0.7 g/L of caffeine.

In still another embodiment of the present invention, the growth time may be in the range of 26–70 hr under agitation at 40–210 rpm.

In still another embodiment of the present invention, the medium for induction may include 30–70 g/L of disodium hydrogen orthophosphate septahydrate, 5–20 g/L of potassium dihydrogen orthophosphate, 0.5–7 g/L of sodium chloride, 1–8 g/L of ammonium chloride and 0.08–0.7 g/L of Caffeine.

In yet another embodiment of the present invention, 0.08–2 g/L of caffeine may be completely removed from 8–30 ml of the solutions by 0.5–4 gm wet weight of the microbial cells in a period ranging from 1–14 hours.

A general process for the bio-decaffeination of caffeine containing solutions is given in the following flow sheet:

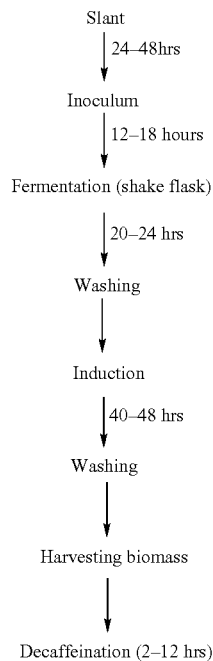

The following examples are given by way of illustration of the present invention only and should not be construed to limit the scope of the invention.

EXAMPLE-1

After screening of various microorganisms isolated from coffee processing wastes, a bacterial culture is selected on the basis of caffeine degrading ability in a well-defined liquid media containing caffeine. Isolation of the microorganism was done by mixing one gram of soil sample with 100 ml of caffeine liquid medium in a 250 ml flask and incubation for 72 hrs at 30° C. in an orbital rotary shaker set at 150 rpm. Caffeine agar medium was prepared and poured into petri plates. Then ten-fold serial dilutions ($10^{-1}$ to $10^{-9}$) of the above grown culture were made and 0.1 ml of the dilutions was inoculated on to each plate and incubated at 37° C. for 2 days.

Isolated colonies growing on the above plates were selected and purified further to obtain pure cultures. On the basis of colony morphology, well-separated colonies of the caffeine degrading bacteria formed on incubated caffeine agar plates were selected and transferred aseptically into fresh caffeine agar plates and incubated at 30° C. for 72 hours. The organism is maintained by sub culturing on caffeine agar slants every 30 days. The bacteria is characterized by morphological, cultural and biochemical tests. The tests included Gram's reaction, catalase production, oxidase production, nitrate reduction, indole production, methyl red test, voges proskauer test, starch hydrolysis, citrate utilization, oxidation, fermentation of sugars, motility, malonate utilization, arginine dihydrolase activity, gelatin liquefaction, growth at 4° C. and 41° C., acid slant, acid butt, alkaline slant, alkaline butt, $H_2S$ production, gas production, urease production, dextrose utilization, mannitol utilization and polyhydroxy alkanoate accumulation and the results are shown in table 1.

The taxonomic features of the bacteria, *Pseudomonas alcaligenes* are summarized as follows: The bacterial colonies were round, small, raised and smooth and microscopic observation revealed that the bacteria were Gram-negative coccobacilli. The cultural and biochemical tests carried out for the identification of the isolate and the results are given in Table. 1.

TABLE 1

Cultural and biochemical tests for the identification of the isolate.

| Biochemical Test | Result |
| --- | --- |
| Catalase | + |
| Oxidase | − |
| Nitrate reduction | − |
| Indole Production | − |
| Methyl red test | − |
| Voges Proskauer test | − |
| Starch hydrolysis | − |
| Citrate utilization | + |
| Oxidation | + |
| Fermentation | + |
| Motility | + |
| Malonate Utilization | + |
| Arginine dihydrolase | + |
| Gelatin hydrolysis | − |
| Growth at 41° C. | + |
| Growth at 4° C. | − |
| Acid slant | − |
| Acid butt | − |
| Alkaline slant | + |
| Alkaline butt | + |
| H2S production | + (Weak) |
| Gas production | − |
| Urease | + |
| Dextrose utilization | − |
| Mannitol utilization | − |
| Polyhydroxy alkanoate (PHB) accumulation | − |

+, Positive for growth;
−, negative for growth;

The isolate is positive for catalase production. Isolate is negative for oxidase production, nitrate reduction, indole production, methyl red test, voges proskauer test and starch hydrolysis. Isolate is positive for citrate utilization, oxidation, fermentation of sugars, motility, malonate utilization, arginine dihydrolase activity, negative for gelatin hydrolysis. The isolate showed growth at 41° C. and growth is inhibited at 4° C. The isolate tested negative for Acid slant and butt, positive for alkaline slant and butt. The isolate is found to be a weak hydrogen sulphide producer. The isolate showed no gas production. The isolate tested positive for urease production and tested negative for dextrose utilization, mannitol utilization and polyhydroxy alkanoate production.

On the basis of morphological, cultural and biochemical characteristics, the isolate is identified as *Pseudomonas alcaligenes* and designated at CFR1708, and deposited at the Microbial Type Culture Collection and Gene Bank, Institute of Microbial Technology, Sector 39-A, Chandigarh 160036, India. The isolate was received for deposit on Feb. 24, 2006 and the accession number is MTCC 5264.

EXAMPLE-2

A loop full of actively growing culture of *Pseudomonas alcaligenes* is transferred to 100 ml of nutrient broth containing 0.3-g/L caffeine and incubated at 30° C. in a rotary shaker at 120 rpm for 24 hrs. 5 ml of the 24 hrs grown pre inoculum is transferred to 100 ml of nutrient broth containing 1 g/L caffeine and incubated at 30° C. for 48 hours on the rotary shaker. Biomass accumulated for 24 hours is harvested by centrifugation for 20 min in a bench top centrifuge at 16,000-x g at 4° C.

This biomass is aseptically transferred into a 500 ml flask containing 100 ml of Caffeine liquid medium containing 0.5-g/L g of caffeine and incubated at 30° C. on the rotary shaker for 48 hrs; 1 gm wet weight of the pellet of above induced biomass is suspended in 2 ml of 0.1 M phosphate buffer. This suspension is then added to a flask containing 10 ml of caffeine liquid medium containing 1 g/L caffeine adjusted to a pH of 5.0 and incubated at 30° C. under agitation on a rotary shaker at 120 rpm. 1 ml aliquots of the medium are drawn at 2, 4, 6, 12 and 24 hours intervals, subjected to centrifugation at 16,000-x g for 10 minutes at 40° C. and analyzed by high performance liquid chromatography for caffeine content. There is a rapid degradation of caffeine, increasing from 54% at 2 h to 96% in 6 hours of incubation (FIG. 1).

EXAMPLE 3

The cultivation of the organism is carried out as in example 1. However, the pH of the medium for decaffeination is adjusted to 6.0. The degradation of caffeine is much more efficient than at pH 5, giving values of 94.5% at 2 hrs and 98% at 6 hours of incubation (FIG. 1).

EXAMPLE 4

The cultivation of the organism is carried out as in example 1. However, the pH of the medium for decaffeination is adjusted to 7.0. Caffeine is completely removed from the solution within 2 hours of incubation (FIG. 1).

EXAMPLE 5

The cultivation of the organism is carried out as in example 1. However the pH of the medium for decaffeination is adjusted to 8.0. 99.3% of the caffeine is removed from the solution within 2 hours of incubation (FIG. 1).

The novelty of the present invention is to completely degrade caffeine rapidly and completely using a microbial culture grown in a synthetic liquid medium.

The Main Advantages of the Present Invention are:

Degradation of caffeine occurs in the neutral pH range i.e., 7.0–8.0.

It is a rapid decaffeination method and completely degrades caffeine within 2–12 hours of incubation.

It avoids the use of hazardous organic solvents for the removal of caffeine.

It employs simple and inexpensive media for the cultivation of a culture of *P. alcaligenes* for the degradation of caffeine.

Prevents the loss of flavour elements and oils from the caffeine containing solutions.

Expedites the decaffeination.

Extremely economical.

Easy to perform and not at all labour intensive.

Cells of the fungus of the instant application grow very fast unlike cells of the prior art.

Accumulation of caffeine free product is high.

The decaffeinated product is commercially useful.

Does not require co-factors (usually unstable) for decaffeination.

The invention claimed is:

1. A simple, safe, and efficient process for the complete bio-decaffeination of caffeine-containing solutions using strain *Pseudomonas alcaligenes* CFR 1708, said process comprising steps of:
   a. culturing the strain in caffeine agar plates,
   b. transferring actively growing culture into nutrient broth containing 0.1–0.5 g/L caffeine,
   c. incubating culture of step (b) at about 28–30° C. for about 20–24 hrs under agitation of between about 50–200 rpm to obtain pre-inoculum,
   d. transferring the pre-inoculum to nutrient broth comprising about 0.5–2 g/L caffeine,
   e. incubating the pre-inoculum at about 28–30° C. for about 20–24 hours under agitation between about 50–200 rpm to accumulate biomass,
   f. harvesting the biomass by centrifugation for about 10–20 mm at about 10,000–16,000 g at temperature ranging between about 0–4° C. to obtain pellet,
   g. inducing the pellet for caffeine degradation by aseptically transferring the pellet into sterilized caffeine liquid medium of pH about 5–9,
   h. incubating the induced pellet at about 25–35° C. under agitation between about 50–200 rotations per minute for time duration of about 36–60 hours, and
   i. decaffeinating caffeine-containing solution by incubating with the pellet of step (h).

2. A process, as claimed in claim 1, wherein concentration of caffeine in nutrient broth is ranging between 0.2–0.4 g/L.

3. A process as claimed in claims 1, wherein the sterilized caffeine liquid medium comprises about 40–60 g/L of disodium hydrogen orthophosphate septahydrate, about 10–15 g/L of potassium dihydrogen orthophosphate, about 1–5 g/L of sodium chloride, about 2–7 g/L ammonium chloride, and about 0.1–0.5 g/L Caffeine.

4. A process as claimed in claims 1, wherein the induction time is ranging between about 40–48 hr.

5. A process as claimed in claim 1, wherein the concentration of caffeine in caffeine-containing solution is ranging between about 0.01–5 g/L of caffeine.

6. A process as claimed in claim 1, wherein the caffeine degradation is complete in about 1–14 hours.

7. A process, as claimed in claim 1, wherein incubating at temperature ranging between 28–30° C. occurs in step (i).

8. A process as claimed in claim 1, wherein the nutrient broth comprises about 0.5–4 g/L of yeast extract, about 3–8 g/L of peptone, about 3–8 g/L of sodium chloride, and about 0.08–0.7 g/L of caffeine.

9. A process as claimed in claim 1, wherein the sterilized caffeine liquid medium has a pH of about 9.

* * * * *